United States Patent [19]

Wen

[11] Patent Number: 5,198,230

[45] Date of Patent: Mar. 30, 1993

[54] COMPOSITION CALLED DTS (DEITIES) FOR THE TREATMENT OF ADDICTIVE DISEASE

[76] Inventor: Liu C. Wen, Flat A2, 6/F., Flora Garden, 50, Cloud View Road, Hong Kong, Hong Kong

[21] Appl. No.: 638,780

[22] Filed: Jan. 8, 1991

[30] Foreign Application Priority Data

Jan. 8, 1990 [CN] China ............................. 90100203.8

[51] Int. Cl.$^5$ .................... A61K 35/12; A61K 35/78; A61K 33/36

[52] U.S. Cl. .................................. 424/525; 424/537; 424/538; 424/551; 424/195.1; 424/653; 424/629; 514/216; 514/266; 514/562; 514/690; 514/692; 514/810

[58] Field of Search .............. 424/95, 195.1, 525, 424/537, 538, 551; 514/810

[56] References Cited

U.S. PATENT DOCUMENTS 5,026,697  6/1991  Lotsof ................................ 514/214
5,028,611  7/1991  Halikas ............................... 514/277

OTHER PUBLICATIONS

Goodman & Gilman—Pharmacological Basis of Therapeutics—8th ed., Pergamon Press, N.Y. p. 561 (1982).

*Primary Examiner*—Frederick E. Waddell
*Assistant Examiner*—Diane Gardner
*Attorney, Agent, or Firm*—Barry Evans

[57] ABSTRACT

This invention provides a recipe for making a detoxification medicine named DTS (Deities) for curing drug addiction. This DTS (Deities) medicine comprises no narcotic but mainly is made up by several kinds of effective ingredients of biological substances refined from various natural herbs and bioproducts. Drug addicts can be weaned and cured safely from addiction induced by Heroin, Cocaine, Morphine, Amphetamines, Hemp or Opium, and other substances within 7–30 days, by means of DTS (Deities) which can get rid of drug poisons present in an addict's blood and marrow. Further, DTS (Deities) can also be used to clear away tobacco tar and nicotine deposits so that it serves to wean from cigarette smoking as well.

8 Claims, No Drawings

COMPOSITION CALLED DTS (DEITIES) FOR THE TREATMENT OF ADDICTIVE DISEASE

FIELD OF THE INVENTION

This invention comprises a composition called DTS (Deities), for the treatment of addictive disease. DTS is mainly comprised of several kinds of effective ingredients of biological substances refined from various natural herbs and bio-products, without any narcotic or stimulant drugs, and methods of making and using same.

BACKGROUND OF THE INVENTION

As is well known, addictive disease of all kinds has been a problem throughout the world since time immemorial. The problem has become more serious in recent years as increasingly more powerful and addictive substances become the drugs of choice for rich and poor alike around the world. One Japanese press report estimated that there were 14.5 million people using illicit drugs in the United States during the year 1988. Similarly, an article published in the "China News Agency" has stated that the United States has 6 million people suffering from addictive disease who are awaiting immediate treatment. Further, according to the 16th issue of "World Knowledge", the Soviet Union has 1.5 million addicts. The list of places suffering from the problems caused, directly or indirectly by addictive diseases includes, Columbia, Hong Kong, Afghanistan, Italy, and India. It is said that the number of addicts all over the world is more than 50 million. In China, an investigation in a north-west city showed that actual number of addicts in one district of this city was over 10,000 in spite of the official (registered) figure of only 700. Investigation was also done in another district of this same city and 5,000 and 2,000 addicts were found in two big enterprises respectively. In remote districts, drug-taking is very open. One can easily meet people taking drugs in restaurants and hotels.

It is been alleged that the number of addicts all over the world is more than 50 million. Drug abuse is a long-standing problem which creates many other social dislocations. In many countries, more than half of criminals have a history of substance abuse. Recent press reports have suggested that this ratio approaches 82% in Philadelphia. In the Soviet Union, it has been stated that quite a few gangs of juvenile delinquents among the thousand gangs cracked down on in 1988 were linked together because of narcotics. In Columbia, since 1984, thousands of those opposing drug dealing have been killed by the drug gangs, including presidents of the country, legislators, senior police officers, news reporters and many others.

Narcotics such as heroin, cocaine, morphine and its derivatives produce both behavioral and physical dependance. These substances excite the cerebral cortex and provide an illusion of happiness and well being which is the basis for the behavioral addiction. Depending upon the particular substance of abuse, the symptoms may include depression, inability to work, loss of appetite, weight loss, insomnia and tiredness, and trembling. Sudden withdrawal can induce prostration and even death.

Narcotics destroy the adrenaline enzyme, and reduce the sensitivity of the nervous system. The only organ of the human body able to eliminate narcotics is the liver. However, it takes at least 60 minutes for the liver to eliminate a lethal dose. Excess quantity is diluted into the blood and then is absorbed into the bone marrow. Some is discharged by the kidney. If an addict stops taking "drugs", 5-8 hours later, he or she begins to face the so-called phenomenon of withdrawal: the victim becomes exhausted and depressed, but in an exciting state, repeatedly crying, yawning, sneeze, snivel, cold sweating, extremely pain in the bones, vomiting, diarrhea, loss of appetite, and loss of will, and a craving for narcotics. It is common knowledge that many addicts will do anything to obtain relief from withdrawal, including committing murder or suicide. To avoid the symptoms of withdrawal, addicts have to consume a sufficient quantity of narcotics.

It is very clear that narcotics are a health hazard. Unfortunately, no safe and effective cure has been found. Methadon treatment is not a cure for addiction. In the United States one method of treatment is to change all the blood of an addict, but this is not a cure, it just serves to maintain life. Because of the serious problem of drug abuse in the United States, President Bush has proposed to provide $7.9 billion for drug enforcement, including $925 million to be used for medical treatment for addicts. President Bush also proposed extensive research to find a cure for addiction. In China, the Ministry of Hygiene provides prescriptions for treatment of addiction which are numbered as 1, 2, 3 and 4. Prescriptions 1, 2 and 3, contain narcotic at gradually reducing quantities. Prescription 1 can be mixed with narcotics and placed on tinfoil paper for smoking. Prescription 4 is only for consolation, so it is actually illegal for sale but must be used under guidelines. However, when the effect of the medication has passed, the symptoms of withdrawal will occur again. Since the Opium War, there have been some methods for treating addiction prevalent in China, listed as follows:

1. Agalloch, Tea, Lotus seed, Jindan to produce a sweetened pill weighing one qian (5 grams) for swallowing.
2. Abrade Radix polygoni mutiflori, Cinnamon Bark, Green tea, Human skull, Astragalus membranaceous, and Hung-Sae-Dan into powder and swallow with boiled water.
3. abrade Lotus seed and mix with opium ash, then swallow with boiled water.
4. six Aconitum carmichaeli, Flow Daturae, Buthus martensii karsch, Cinnbaris, which are herbs of prisoners, and swallow.
5. mix Lu-Shen-Wan, Jindan, Chlorpromazinum, and swallow.

However, all of the above medicines are unsafe for use in treating addiction. The above compositions often killed addicts utilizing them.

As has been described, at present there is no satisfactory cure for addictive disease. Thus, it can be readily appreciated that a method of treating and curing those who suffer from addictive disease, utilizing a composition having no narcotic ingredients, which can effect a cure within a range of 7-30 days and clear all drug deposits from an addict's blood and marrow, would be of great benefit to the entire world.

OBJECTS OF THE INVENTION

It is an object of the invention to provide a composition for the treatment of drug addiction and a method of making and using the composition.

SUMMARY OF THE INVENTION

In one embodiment, the invention comprises a composition for treating the symptoms of withdrawal from addictive substances called DTS comprising the ingredients of: 25% Zanthoxylum nitidum or Cordyceps powder, 15% Datura stramonium or Flos Daturae Powder, 10% Aconitine powder, 10% Cystine powder, 10% Bungarus powder, 6.5% Scolopendra powder, 5% Scorpions powder, 4.5% Officinale baill powder, 4% Bismuthi subnitras powder, 3% Realgar powder, 2.5% Licorice root acid, 2% Angelica siniensis powder, 1% Ox gallstone or Bilirubin powder, 0.5% Toad powder, 0.5% Muskone, 0.3% Aeropinum, and 0.2% D. Camphora colebr.

In a further embodiment, the invention comprises a composition called DTS for treating the symptoms of withdrawal from addictive substances produced by the steps of: combining 25% Zanthoxylum nitidum or Cordyceps powder, 15% Datura stramonium or Flos Daturae Powder, 10% Aconitine powder, 10% Cystine powder, 10% Bungarus powder, 6.5% Scolopendra powder, 5% Scorpions powder, 4.5% Officinale baill powder, 4% Bismuthi subnitras powder, 3% Realgar powder, 2.5% Licorice root acid, 2% Angelica siniensis powder, 1% Ox gallstone or Bilirubin powder, 0.5% Toad powder, 0.5% Muskone, 0.3% Aeropinum, and 0.2% D. Camphora colebr where each powder is finer than 300 mesh; compounding the ingredients of 'a' by crushing together to a fine powder with a mortar; killing substantially all bacteria present by illumination with an ultra-violet-lamp for 6 hours; spraying boiled honey water (50%) on the powder of 'c' until honey forms 15% of the total quantity; stirring in a vacuum stirrer for one hour; and forming tablets or capsules.

In yet a further embodiment, the invention comprises a method of treating substance addiction by administering DTS 2-3 grams every six (6) hours.

In still a further embodiment, the invention comprises a method of treating tobacco addiction comprising administering DTS 0.2-0.5 grams whenever the desire to smoke is manifested.

In still a further embodiment, the invention comprises a method of treating substance addiction comprising the steps of: obtaining ingredients: Zanthoxylum nitidum (25% of a recipe), Datura stramoniun (15%), Aconitine (10%), Cystine (10%), Bungarus Multicinctus (10%), Scolopendra (6.5%), Scorpion (5%), Officinale Baill (4.5%), Bismuthi subnitras (4%), Realgar (3%), Licorice Root acid (2.5%), Angelica Siniensis (2%), Ox gallstone (1%), Muskone (0.5%), Bufotoxin (0.5%), Aeropinum (0.3%) and D. Camphora Colehr (0.2%); crushing the ingredients to powder and mixing; adding honey up to 15% of the total quantity to the powder of c to form a mix; forming the mix into tablets or capsules.

DETAILED DESCRIPTION OF THE INVENTION

Pharmacological Principles

The only organ of human body able to eliminate drugs is the liver, yet its ability is very limited. Additionally, addicts usually have a poor appetite, which further weakens the function of the liver. The only material to strengthen the detoxification function of the liver is cystine. However, that substance is usually scarce inside human body. Cystine is in fact a crucial element to cure liver disease. Besides, Licorice Root acid is effective to detoxify many kinds of poisons in traditional Chinese herb medicine because it has the effect to enhance the enzyme of adrenaline and has ACTH biologically active material which enhances metabolism, so as to detoxify cocaine effectively.

However, an addict has greater resistance to an anaesthetic, more than multiple-ten-times than that of ordinary people, e.g. a one-year-history-addict will not fall asleep even taking 20 sleeping pills. Clinical trials have proved that "Spasmedal" is the substance which functions to calm an addict. Yet taking "Spasmedal" for long time forms habit too. Using two kinds of Chinese herbs, Datura Stramonium and Angelica Siniensis together can anaesthetize, at enough quantity, a patient for a surgery. However, precaution must be taken when anaesthetizing an addict because he is usually too weak to be anesthetized. When using Chinese herb for anaesthesia, a kind of herb which is alleged in Chinese traditional medicine be effective "to restore Yang (i.e vital function) from collapse", e.g. Aconitum carmichaeli seems very necessary to be used as well.

But to calm an addict is only the first step, next it is required to clear away intrinsic narcotic resided in blood and marrow so as to permit an addict to recover and live a normal life. As a matter of fact, an addict, having taken rough-refined-heroin and cocaine for a long time, would have ulcerated skin something like a leper at the late stage of disease. The phenomenon is due to toxic effects upon the blood and marrow. According to the traditional Chinese recipe and experiment, Bungarus multicinctus is an effective medicine.

Because this invention involves a mixture of 18 kinds of ingredients the pharmaceutical function is very complicated. After two hundred and some clinical observations and practices, its major functions are summarized as to: (1) limit endocrine glands; (2) release pain by anaesthesia; (3) clear away, with the help of its ingredients i.e. The poison of Snake and Bufotoxin (biological poisonousness), the original shapes of drugs present in blood and marrow through excretion and aspiration out of skin; (4) maintain continuous movements of addicts' stomachs and intestines so as to create hungry feelings and to maintain normal excretion, here Officinale baill is an ideal ingredient.

Hence, taking DTS(Deities) 2-3 grams orally every six (6) hours, one can be cured by eliminating the phenomenon of withdrawal and addiction.

In addition, experiments have proven that DTS(Deities) can also be used to get rid of tar, nicotine's deposit inside one's body and to make one dislike cigarette smoking so as to serve the purpose for weaning cigarette smoking as well. In this case, one should take 0.2-0.5 grams each time whenever one has the desire to smoke.

To further clarify the pharmacology of this invention, the functions of each ingredient are listed as follows:

1. Zanthexylum nitidum: release pain, such as tooth-pain, nervous pain, rheumatic pain, substitute for Dicaine for local anaesthesia operation and anti-cancer.
2. Datura stranonium: relieve convulsion, analgesia, pease sleep, used with angelic siniensis for general anaesthesia.
3. Aconitum carmichaeli: release pain, cure prostration, limbs chilling and strengthless.
4. Cystine: enhance cell-metabolism, improve liver's function, enhance white blood cell, detoxify.

5. Bungarus multicinctus: stop convulsion, capture toxity.
6. Scolopendra: relieve rheumatics, stop convulsion, capture toxity and cure ulcer.
7. Scorpion stop convulsion, cease rheumatics, capture toxity.
8. Officinale Baill: good for digestion, dissolve extra vasated blood, stimulate peristalsis of stomach and intestines easy excretion.
9. Bismuthi Subnitras: form a protective coating on walls of stomach and intestines to resist excitement by drugs.
10. Realgar: smooth spirit, detoxifying.
11. Licorice Root acid: detoxifying, enhance metabolism.
12. Angelic siniensis: invigorate the circulation of blood, relieve pain.
13. Ox Gallstone: detoxifying, analgesia
14. Muskone: good for brain function, invigorate the circulation of blood and body fluid, diminish the size of small tumors and relieve pain.
15. Bufotoxin: stimulate the circulation of blood and cause the muscles and joints to relax, capture toxity.
16. Aeropinum (or Flos Daturan): control secretion of glands, eliminate inhibition to breath caused by morphine and its likes, release inhibition to heart by vagus.
17. D. Camphora Colebr: Wake the patient from unconsciousness, relieve pain.
18. Honey: good to lungs, intestines, and as excipient.

Most of the above ingredients are biological toxins. According to the assumption of active element of biological carrier in Chinese herb pharmacology, i.e. The mutual action between the medicine and symptoms gives a co-ordinative and repellent effect to an addict's nervous system. The principal, adjuvant, auxiliary and conductant ingredients in the prescription are described as follows: The principal ingredient provides the principal curative action. The adjuvant helps strengthen the principal action, the auxiliary and correctant ingredient relieves secondary symptoms or tempers the action of the principal ingredient when the later is too potent. The conductant directs action of the affected channel or site), this medication restores Yang, (i.e. protects a vital function from collapse), provides calm, pain-release and detoxification.

The features and aspects of this invention will be more fully explained by way of the following examples.

Example 1. Preparation of the DTS (Deities) Composition

Clean the root or the skin of root and stalk of Zanthoxylum nitidum, slice, sun-dry or bake-dry at 60° C., crush to powder finer than 300-mesh. Portion of this ingredient is 25%.

Use fresh flower, beginning bloom, of Datura Stramonium, bake-dry at 60° C., crush powder finer than 300-mesh, (which has a composition of 0.215% of Tropine). Portion of this ingredient is 15%.

Clean & slice Aconitum Carmichaeli, cook for 90 minutes under 1.5 kg/cm pressure and at 122° C. This can dissolve its toxic fat into water. Aconitum Carmichaeli is then of 0.72% Aminealcohol Alkaloid. Bake-dry at 60° C., crush to powder finer than 300-mesh. Portion of this ingredient is 10%.

Place hair into 70°-80° C., 8.9-9 N HCL solution, raise temperature of 110°-117° C. for 6.5 hours to obtain filtered solution, add NaOH solution (30-40%) into the filtered solution till pH value reaches 4.8. Put aside for 36 hours, dehydrate by centrifugation to obtain rough cystine. Put it into 10 N HCL solution, add activated carbon to decolour, obtain filtered solution by press-filtration, add NaOH solution (30%) till pH value reaches 4.8, place aside till crystal deposit appears, pour away the solution and fill back HCL solution (1 N), add activated carbon again to decolour, then neutralize with ammonia water till PH value reaches to 3.5-4.0. In this way crystallized cystine with content of more than 90% is obtained. Finally wash with pure water to remove chlorine, dry by vacuum, crush to powder finer than 300-mesh. Portion of this ingredient is 10%.

Obtain living Bungarus in summer and autumn respectively, take away blood, bake-dry at 60° C., crush to powder finer than 300-mesh. Portion of this ingredient is 10%.

Obtain living Scolopendra in spring and summer respectively. Use boiling water to kill, bake-dry at 60° C., crush to powder finer than 300-mesh. Portion of this ingredient is 6.5%.

Obtain Scorpions during end of spring and beginning of autumn respectively. Put into salted or ordinary water, boil until the body become stiff and the abdomen hard. Remove the bones on their backs, bake-dry at 60° C., crush to powder finer than 300-mesh. Portion of this is 5%.

Obtain roots and stalks of officinale Baill of age over 3 years during end of Autumn and beginning of Winter, take away leafs and root hairs, peel off skin, slice, bake-dry at 60° C., crush to powder finer than 300-mesh, portion of this ingredient is 4.5%.

Crush crystals of Bismuthi subnitras to powder finer than 300-mesh. Portion of this ingredient is 4%.

Crush medical grade Realgar to powder finer than 300-mesh. Portion of this is ingredirnt is 3%.

Soak Licorice Root in water, obtain the solution and add sulfuric acid till PH value reaches 1.8, which precipitates Licorice Root, pour away clean water and use tap water to wash away residue sulfuric acid, add ammonia water (25%) till PH value reaches to 7.0, then Ammonia Glycyrrhetate with content higher than 60% is obtained. Place on glass plate to dry and then crush to powder finer than 300-mesh. Portion of this is 2.5%.

Hang Angelica siniensis, half-dried by wind or stored, use gentle fire to dry at 60° C., crush to powder finer than 300-mesh. Portion of this ingredient is 2%.

Crush Ox Gallstone, artificial Ox Gallstone or Bilirubin to powder finer than 300 mesh. Portion of this is 1%.

Obtain Toad during spring and autumn respectively. After cleaning, extrude gland's at ear-back and skin to obtain white liquid, put this white liquid on glass plate and bake-dry at 60° C. Portion of this is 0.5%.

Portion of Muskone is 0.5%.
Portion of Aeropinum or Flos Daturae is 0.3%.
Portion of D. Camphora colebr is 0.2%, put this together with muskone, Bufotoxin, Aeropinum (Flow Daturae) into a mortar and crush to fine powder.

Finally use ultra-violet-lamp to shine on all materials to kill bacteria for 6 hours, spray boiled honey water (50%) on to above mentioned powder. Quantity of honey sprayed is 15% of the total quantity, place all materials into a vacuum stirrer and stir for one hour. Use palleting (tableting) machine to produce pallets (tablets) or make into capsules, or alternatively add 20-40% cocoa powder to produce chocolate candy and pack.

Characteristics of this product

Pallet (tablet) is brown-yellow (with or without outside coatings), chocolate is dark brown, strong smell or fragent, taste sweet, spicy and refreshing.

Example 2. Method for distinguishing the DTS (Deities)

Composition

A. Microscopic Method

Upon lacing the powder of this invention under a microscope, one can observe thick and short pipes colored yellow and with furrow lines, fibers are colorless in bunches with pointed terminals, having some very short branches with rough edges, diameter is about 100 μm, pipes with mesh one of 12-48 μm in diameter. Flower grains are colorless or light yellow, shaped as a ball or a flat ball, diameter of 45-68 μm. Holes are not obvious, outer walls with nuclear strips, the epidermis cells of corolla are observed from surface as shaped as squares and undulant curves with long round gas holes on the top. There are lots of starch grains, single grains shapes as ball, long round, umbilicus, herringbone or trident and some of them with duplicate grains of 3 sub-grains.

B. First Chemical Method

Place 0.5 gram powders of this product into 10 ml of 1/10 N Liquid hydrochloric acid, shake well and rest for 30 minutes; filter the mixed liquid and obtain 1.5 ml of the filtered liquid, add 6-7 drops of 2× Ethanolninhydrin into the liquid, heat 5-6 minutes to boil, then the color of liquid turns to orange red.

C. Second Chemical Method

Place 0.5 gram powders of this product into 10 ml of Ethanol, shake well and put aside for one hour. After filtration, add 1-2 drops of Potassium-Iodohydrargyrate, yellow deposits can be observed.

What is claimed is:

1. A composition for treating the symptoms of withdrawal from addictive substances comprising 25% Zanthoxylum nitidum or Cordyceps powder, 15% Datura stramonium or Flos Daturae Powder, 10% Aconitine powder, 10% Cystine powder, 10% Bungarus powder, 6.5% Scolopendra powder, 5% Scorpions powder, 4.5% Officinale baill powder, 4% Bismuthi subnitras powder, 3% Realgar powder, 2.5% Licorice root acid, 2% Angelica siniensis powder, 1% Ox gallstone or Bilirubin powder, 0.5% Toad powder, 0.5% Miskone, 0.3% Aeropinum, and 0.2% D. Camphora colebr.

2. A composition as recited in claim 1 compounded with boiled honey to form a final composition comprising 15% honey.

3. A composition as recited in claim 2 compounded with cocoa powder to form a final composition comprising 20-40% cocoa.

4. A process for manufacturing a composition for treating the symptoms of withdrawal from addictive substances by the steps of:
   a. combining 25% Zanthoxylum nitidum or Cordyceps powder, 15% Datura stramonium flower or Flos daturae powder, 10% Aconitine powder, 10% Cystine powder, 10% Bungarus powder, 6.5% Scolopendra powder, 5% Scorpions powder, 4.51% Officinale baill powder, 4% Bismuthi subnitras powder, 3% Realgar powder, 2.5 Licorice root acid, 2% Angelica siniensis powder, 1% Ox gallstone or Bilirubin powder, 0.5% Toad powder, 0.5% Muskone, 0.3% Aeropinum, and 0.2% D. Camphora Colebr. where each powder is finer than 300 mesh;
   b. compounding the ingredients of step 'a' by crushing them together into a fine powder with a mortar;
   c. killing substantially all bacteria present by illumination with an ultraviolet lamp for 6 hours;
   d. spraying boiled 50% concentration honey water on the powder of step c until the honey comprises 15% of the total quantity;
   e. stirring the composition in a vacuum stirrer for one hour to form a mixture; and
   f. forming the mixture into tablets or capsules.

5. The process according to claim 4 wherein the mixture formed in step (e), is combined with cocoa powder to form chocolate candy having a composition of 20-40% cocoa powder.

6. A method of treating substance addicted patients comprising administering 2-3 grams of a composition as recited in claim 1 orally every six hours.

7. A method according to claim 6 wherein the addicted patients are dependent upon heroin, cocaine, morphine, amphetamines, hemp, opium or tobacco.

8. A method of treating tobacco addicted patients comprising administering 0.2-0.5 grams of a composition as recited in claim 1 orally whenever the desire to smoke is manifested by said addicted patients.

* * * * *